(12) United States Patent
Barker et al.

(10) Patent No.: US 7,046,358 B2
(45) Date of Patent: May 16, 2006

(54) ELECTRIC FIELD RESONANCE ASSISTED RAMAN SCATTERING FOR LADAR IFF

(75) Inventors: Delmar L. Barker, Tucson, AZ (US); Harry A. Schmitt, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 327 days.

(21) Appl. No.: 10/630,035

(22) Filed: Jul. 30, 2003

(65) Prior Publication Data

US 2005/0024634 A1    Feb. 3, 2005

(51) Int. Cl.
*G01J 3/44* (2006.01)
*G01N 21/65* (2006.01)

(52) U.S. Cl. ...................................... 356/301
(58) Field of Classification Search ................. 356/301
See application file for complete search history.

(56) References Cited

U.S. PATENT DOCUMENTS

| | | | |
|---|---|---|---|
| 5,017,007 A * | 5/1991 | Milne et al. ................. | 356/301 |
| 5,200,606 A | 4/1993 | Krasutsky et al. | |
| 5,255,067 A * | 10/1993 | Carrabba et al. ........... | 356/301 |
| 5,272,351 A | 12/1993 | Andressen | |
| 5,459,470 A | 10/1995 | Wootton et al. | |
| 5,644,386 A | 7/1997 | Jenkins et al. | |
| 5,866,430 A * | 2/1999 | Grow .......................... | 436/172 |
| 6,042,050 A | 3/2000 | Sims et al. | |
| 6,466,710 B1 | 10/2002 | Pergande | |

OTHER PUBLICATIONS

Surface Plasmons and Gratings, Jun. 2001, University of Exeter.
F.J. Garcia-Vidal and J.B. Pendry, Collective Theory for Surface Enhanced Raman Scattering, Aug. 5, 1996, Physical Review Letters vol. 77, No. 6.
Raman Spectroscopy, 2001.
Therm Nicolet Corporation, The History of Raman Spectroscopy, 1995-2000.
Larry G. Anderson, Raman Spectroscopy, 2001.
Shuming Nie and Steven R. Emory, Probing Single Molecules and Single Nanoparticles by Surface-Enhanced Raman Scattering (Publicator and web page provided), Feb. 21, 1997, Science vol. 275.
Kaiser Optical System, Inc., Virtual Raman Tutorial, 2001.

* cited by examiner

*Primary Examiner*—F. L. Evans
(74) *Attorney, Agent, or Firm*—Renner, Otto, Boisselle & Sklar, LLP

(57) ABSTRACT

An identification system for identifying objects of interest is disclosed. The system includes an enhancement mechanism for enhancing Raman scattering from a plurality of Raman active molecules (RAMs). An interrogator transmits a signal toward an object of interest and receives a return signal therefrom. The return signal includes a Raman signature, and the interrogator classifies the object based on the Raman signature.

47 Claims, 13 Drawing Sheets

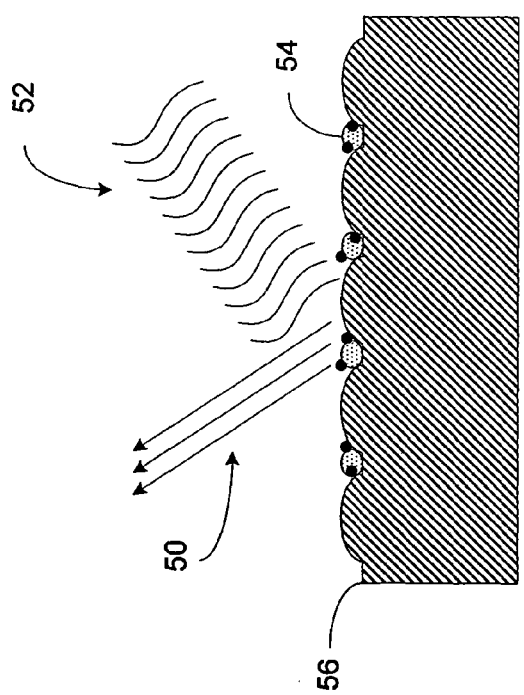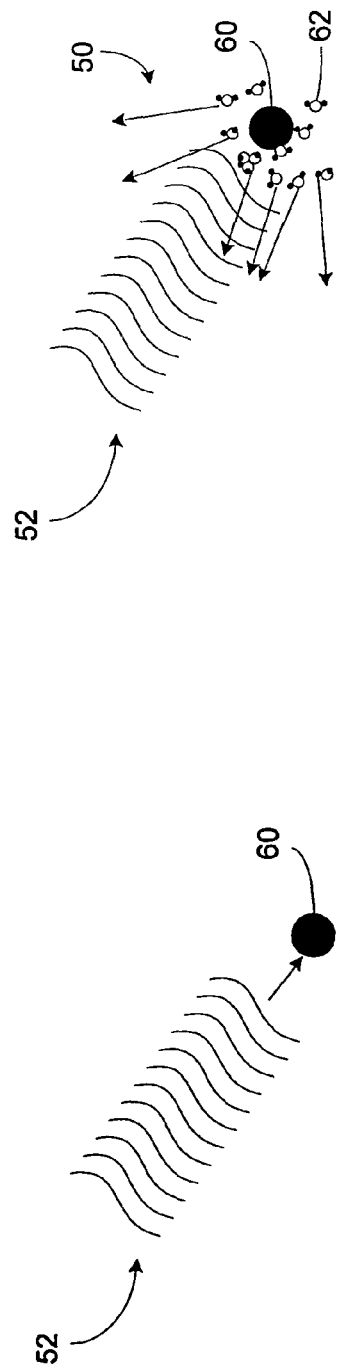

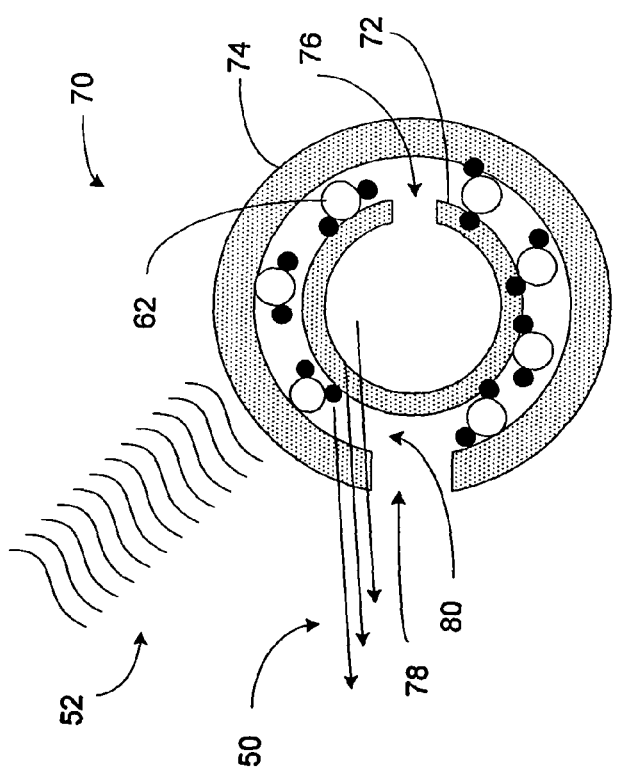
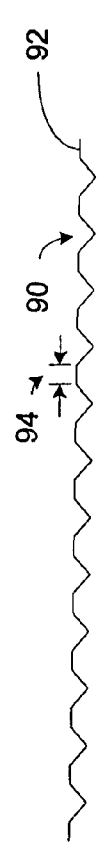
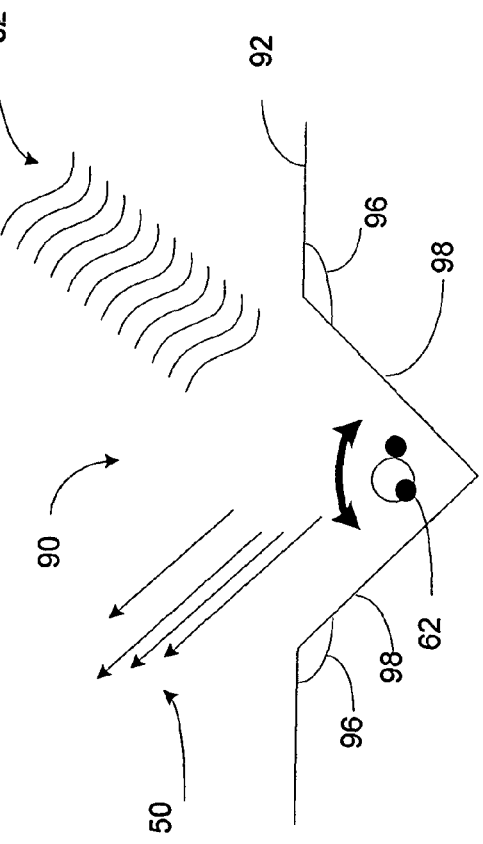
Fig. 5A
Fig. 5B
Fig. 4

ELECTRIC FIELD RESONANCE ASSISTED RAMAN SCATTERING FOR LADAR IFF

FIELD OF THE INVENTION

The present invention relates to identification systems, and more particularly to a system and method to determine the status of a potential target, adversary, or entity using Raman scattering.

BACKGROUND OF THE INVENTION

With the advent of modern warfare, a battlefield has become an even more dangerous place. Unfortunately, this is true both for one's comrades-in-arms as well as for the enemy. Given the amount of firepower deployed in a battle zone, the constant movement of men and material, the rapidity with which tanks, personnel carriers, planes and helicopters move, and the inability to always know (regardless of the amount of effort employed) who is where, the chances of fratricidal harm being inflicted probably are higher than they have ever been. It thus has become imperative to limit, if not altogether eliminate, casualties resulting from "friendly" fire.

One way of discerning who is a friend and who is not is by use of an IFF (Identification Friend-or-Foe) system. Various IFF systems are well-known in the art. These typically are radio frequency (RF) transmission systems and, while principally associated with aircraft, the same technology is applicable to land based vehicles or ships. Certain RF systems, known as co-operative systems, involve transmitting an inquiry signal to an unknown object, e.g., an airplane, ship, tank, etc. If the object is a "friendly", it has some type of transponder for responding to the inquiry with an appropriate reply. Upon receipt of an appropriate reply, the object is designated as friendly. If the object does not provide the required response, it is designated a foe and may be attacked.

Referring to FIG. 1, a battlefield 10 is illustrated in which both friendly and hostile forces are present. The friendly forces include, for example, a first tank 12, a second tank 14, a first personnel carrier 16, a second personnel carrier 18, and an attack plane 20. The hostile forces include a third tank 22, a fourth tank 24, and an attack helicopter 26.

The attack plane 20 carries an interrogator 30, e.g., a first portion of the IFF. The interrogator 30 emits a radio frequency (RF) signal, which generally is coded, on the battlefield. The signal is received and decoded by a transponder 32, e.g., a second portion of the IFF, which is located on (or in) friendly vehicles on the battlefield. In response to receiving the signal, each transponder transmits a signal back to the interrogator 30. If the interrogator 30 receives a proper reply from a vehicle's transponder 32, the vehicle is designated as a friendly. Conversely, if the interrogator 30 does not receive a reply or receives an improper reply from a vehicle's transponder, the vehicle is designated as a foe.

One drawback with co-operative systems is that it always is necessary for the object under inspection to have some mechanism for responding to an interrogation. A second drawback is that while co-operative IFF systems are the most positive types of identification systems and have been employed for a number of years in a variety of forms, they are not infallible. This is so for a number of reasons. For example, the response mechanism on the interrogated object may be inoperative or, because these type systems utilize codes, the code in the response mechanism may not be up-to-date. Consequently, the failure to respond to an interrogation signal cannot always be taken as an indication that the unknown object is hostile. As RF systems, they are vulnerable to jamming, they can be detected from many directions, thereby giving away the location of the weapon platform and, because of the power requirements of RF systems, they tend to be large.

To overcome some of these problems, other means of signal transmission have been employed, such as laser transmission systems. In laser systems, the laser beam replaces the RF as the medium for signal transmission, and the transponder is configured to receive the laser beam (as opposed to an RF signal). As the laser beam strikes the transponder, a portion of the laser beam is reflected back toward the source with a modulated response message. While this configuration is not susceptible to RF jamming, it is not infallible. Malfunctions and/or power loss in the transponder can prevent communications with the interrogator, thus allowing for potential errors in identification.

Another concern in the battlefield is the use of biological and/or chemical weapons. The threat of biological weapons as tools of modern warfare and urban terrorism is increasing. While the exact risks are unknown, the use of biological weapons by military adversaries and/or terrorists potentially could result in life-threatening illness and death on a large scale. Even a lone terrorist could cause a major disease outbreak in the population and, in the case of communicable disease, the outbreak could spread in successive waves of infection.

Unlike explosions or chemical releases, a bioterrorist attack could be surreptitious and thus difficult and time-consuming to detect. Symptoms might not occur among victims for days or weeks, and those initially presenting themselves to physicians and clinics might be geographically dispersed.

Development of early detection, counter measures, and remediation technology is a high priority in many military, government and private laboratories around the world. Biological warfare (BW) agents of critical concern are bacterial spores, such as *Bacillus anthracis* (anthrax), *Clostridium tetani* (tetanus), and *Clostridium botulinum* (botulism). Spores, produced by certain types of gram positive bacteria in response to starvation, are non-growing, heat-resistant, dehydrated, and resistant to extremes of temperature, pH, desiccation, radiation, and chemical agents. Due to their high stability, spores are difficult to stain using typical cell biology methods and, consequently, are challenging to detect and enumerate. This stability and difficulty with conventional detection methods, in turn, make them an attractive tool for use in biological weapons.

An effective bacterial spore detection method must be rapid, sensitive, selective, and cost-effective. In addition to these criteria, the technology must be easily incorporated into a handheld or field-portable device that has low power requirements, requires little maintenance, and provides reliable results.

Presently, vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure.

One particular spectroscopic technique, known as Raman spectroscopy, utilizes the Raman effect. The Raman effect is a phenomenon of inelastic light scattering. When light is scattered from a molecule most photons are elastically scattered, e.g., the scattered photons have the same frequency and, therefore, the same wavelength as the incident photons. A small fraction of light, however, is scattered at optical frequencies different from, and usually lower than, the frequency of the incident photons.

The Raman effect arises when a photon is incident on a molecule and interacts with the electric dipole of the molecule. Generally speaking, the Raman effect is very weak; approximately one photon out of one million will scatter from the sample at a wavelength slightly shifted from the original wavelengths.

Referring to FIG. 2, a significant increase in the intensity of Raman scattering 50 due to incident optical radiation 82 can be observed when molecules 54 are brought into close proximity to (but not necessarily in contact with) certain metal surfaces 56. This increase is known as surface enhanced Raman scattering (SERS). Enhancements by factors of $10^3$ to $10^8$ can be realized in the surface enhanced Raman scattering (SERS) intensity for adsorbates on or near special rough metal surfaces. This phenomenon has been verified for adsorbates at silver, copper, and gold metal surfaces under both solution and vacuum conditions.

It has been experienced, however, that because of the requirement for a metal surface for the SERS effect to be effective, most SERS media have limited usefulness in environments where the compounds do not adsorb easily onto the metal surface. Therefore, it has not been possible to utilize SERS media to monitor exposure to chemical compounds, such as many toxic organics, or biological species, such as bacteria or viruses, which do not adsorb easily onto a metal surface.

Accordingly, there is a need the art for an identification system that can identify biological and/or chemical compounds in a hostile environment as well as a civilian environment. Furthermore, there is a need in the art for an identification system that reliably can classify objects as friend-or-foe without being susceptible to presently known jamming techniques.

SUMMARY OF THE INVENTION

In the light of the foregoing, the invention relates to a system for increasing Raman emissions from a plurality of Raman active molecules (RAMs) and making an identification therefrom, including an enhancement mechanism, wherein the enhancement mechanism enhances Raman scattering from the plurality of Raman active molecules (RAMs); and an interrogator for transmitting a signal toward an object of interest and receiving a return signal therefrom, wherein the return signal includes a Raman signature, and the interrogator classifies an object based on the Raman signature.

Another aspect of the invention relates to a method for increasing Raman emissions from a plurality of Raman active molecules (RAMs) and making an identification therefrom, including the steps of providing an enhancement mechanism, wherein the enhancement mechanism enhances Raman scattering from the plurality of Raman active molecules (RAMs); creating a local electric field about the enhancement mechanism to induce enhanced Raman scattering; and classifying an object based on a Raman signature produced by the enhanced Raman scattering.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 2 illustrates surface Raman scattering on a rough metal surface as known in the prior art.

FIG. 3A illustrates a metal nano-sphere prior to being struck by optical radiation.

FIG. 3B illustrates the metal nano-sphere of FIG. 3A undergoing enhanced Raman scattering due to plasmon resonance after being struck by the optical radiation.

FIG. 4 is a schematic diagram of a split ring resonator undergoing enhanced Raman scattering due to plasmon resonance.

FIG. 5A schematic diagram of a deep grooved metal surface.

FIG. 5B illustrates the deep grooved metal surface of FIG. 5A undergoing enhanced Raman scattering due to plasmon resonance.

DESCRIPTION OF THE INVENTION

Figure 1:
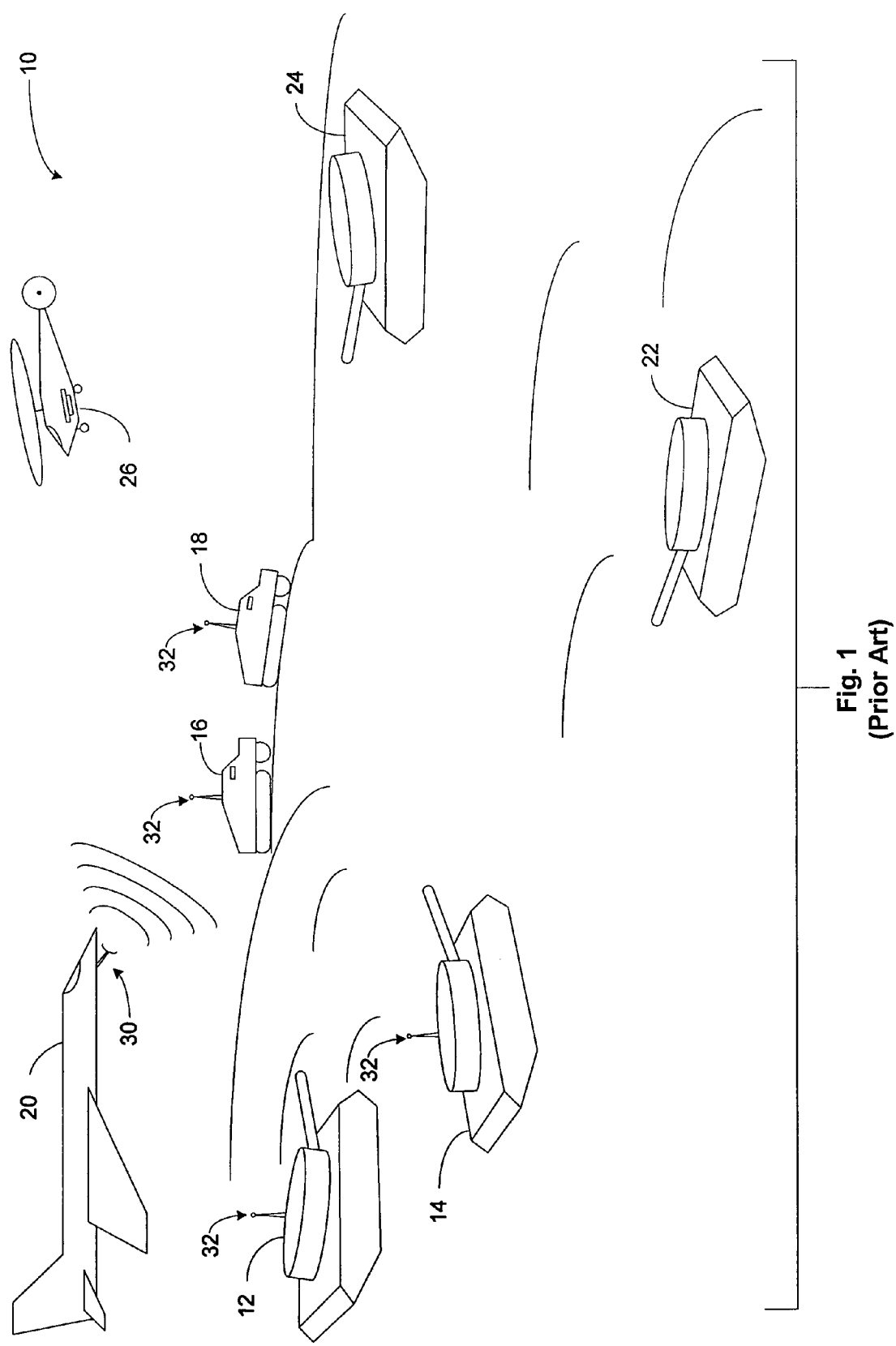
FIG. 1 is a representation of a battlefield environment in which a prior art identification friend-or-foe system is employed.

The following is a detailed description of the present invention with reference to the attached drawings, wherein like reference numerals will refer to like elements throughout.

Raman spectroscopy provides direct information on the vibrational states of molecules in a substance. These vibrational states, as revealed from the main features of the spectrum, provide a "signature" of the different molecules in a mixture; and the intensity of the "peaks" in the spectrum relates to the number of molecules in a particular vibrational state. Using the Raman signature, an object and/or a material may be identified with a high degree of certainty, thus making Raman spectroscopy an attractive means for identification of materials. As described previously, however, the Raman effect is very weak; approximately one photon out of one million will scatter from the sample at a wavelength slightly shifted from the original wavelengths. An object of the invention is to produce enhanced Raman scattering, e.g., an increase in Raman emissions. An increase in the Raman emissions will facilitate the implementation of identification systems based on the Raman effect. The increase in emissions will provide a stronger signal, thereby increasing sensitivity and accuracy of the overall system.

In accordance with the invention, Raman emissions are increased by including an enhancement mechanism along with Raman active molecules (RAMs). RAMs, as are known in the art, are molecules that contribute to Raman scattering or that generate a Raman signal. In one embodiment the enhancement mechanism increases Raman emissions through plasmon resonance.

Plasmon resonance involves surface plasmons, which are transverse magnetic electromagnetic waves that travel along the interface between a dielectric and a metal. These waves are exponentially attenuated in the normal direction and propagate parallel to the interface. A surface plasmon can be generated by the interaction of an electron rich surface, such as that of a metal, with a charged particle or with a photon. When the wavelength of incident radiation is close to the plasma wavelength of the metal, conduction electrons in the metal surface are excited into an extended surface electronic state. Molecules adsorbed or in close proximity to the surface experience an exceptionally large electromagnetic field, and vibrational modes normal to the surface are strongly enhanced. An optimum point is reached wherein the RAMs vibrate substantially in unison, and Raman emissions are maximized.

Referring to FIG. 3A and FIG. 3B, a first enhancement mechanism utilizing metal nano-spheres 60 is illustrated. The metal nano-spheres 60 generally are about one-tenth of the wavelength of the incident radiation in diameter ($\approx \lambda/10$). The nano-spheres, using conventional techniques, can be fabricated using conductive metals such as silver, copper, gold and aluminum, although other conductors can be used. The metal nano-spheres 60 and the RAMs 62 are combined in a common medium to facilitate the application of the RAMs and metal nano-spheres to an object. The number of metal nano-spheres and the number of RAMs combined in the medium depends on the design parameters chosen by the user, such as the intensity of Raman scattering needed or desired. An appropriate quantity of metal nano-spheres 60 and RAMs can be expressed as the ratio $K = S_N/R_N$, where $S_N$ is the number of metal nano-spheres and $R_N$ is the number of RAMs. $R_N$ can have a vast range depending on the application. However, $R_N$ should not be so large as to create a layer over the entire surface of the metal nano-sphere and thus reduce or prevent Raman scattering from taking place.

Enhanced Raman scattering is triggered by incident optical radiation 52, which induces plasmon resonance on the surface of the metal nano-sphere 60. The plasmon resonance creates an intense electric field on and near the surface of the nano-sphere 60 and, as described above, RAMs 62 within the electric field increase their Raman emissions by as much as $10^6$ as compared to RAMs not in the electric field. Additionally, the Raman emissions produce a Raman signature that is shifted in frequency such that it is unambiguous and unique to the particular molecule or combination of molecules chosen for the identification signal. Accordingly, changing the molecule or the combination of molecules changes the Raman signature.

Referring to FIG. 4, another enhancement mechanism utilizing a split ring resonator 70 is illustrated. The split ring resonator 70 includes two concentric metal rings, an inner ring 72 and an outer ring 74. Each metal ring includes an opening 76, 78, and a concentric gap 80 exists between the inner ring 72 and the outer ring 74. RAMs 62 reside within the concentric gap 80. The concentration of RAMs within the ring is chosen such that the concentration does not affect the resonance of the split ring resonator. The overall dimensions of the split ring resonator 70 are controlled by the RAM wavelength. For example, the ring radius is on the order of $\lambda/5$. The metal rings may be formed using conventional techniques from any good conductor such as, for example, silver, gold, aluminum and copper.

Incident optical radiation 52 excites the split ring resonator 70 triggering plasmon resonance, which generates strong electric fields in the concentric gap 80. As discussed above, RAMs 62 within the range of the electric field undergo enhanced Raman scattering 50

Referring to FIG. 5A and FIG. 5B, another enhancement mechanism utilizing deep grooved metal gratings 90 is illustrated. Deep grooves 90 are dispersed along a metal surface 92. Generally, the grooves are formed in a uniform pattern to achieve a cooperative action, and are spaced apart by a factor of the wavelength of the incident radiation ($\lambda$), for example. The metal gratings, using conventional techniques, can be formed from silver, gold, copper and aluminum, for example, and RAMs 62 are placed in the deep metal groove 90. It is noted that the densities of the surface of the metal groove should not exceed a few atomic radii.

Incident optical radiation 52 triggers plasmon resonance in the deep grooved metal grating. The plasmon resonance concentrates a strong electric field deep in the groove 90, and RAMs 62 within the electric field increase their Raman emissions, thereby producing enhanced Raman scattering 50.

Figure 6:
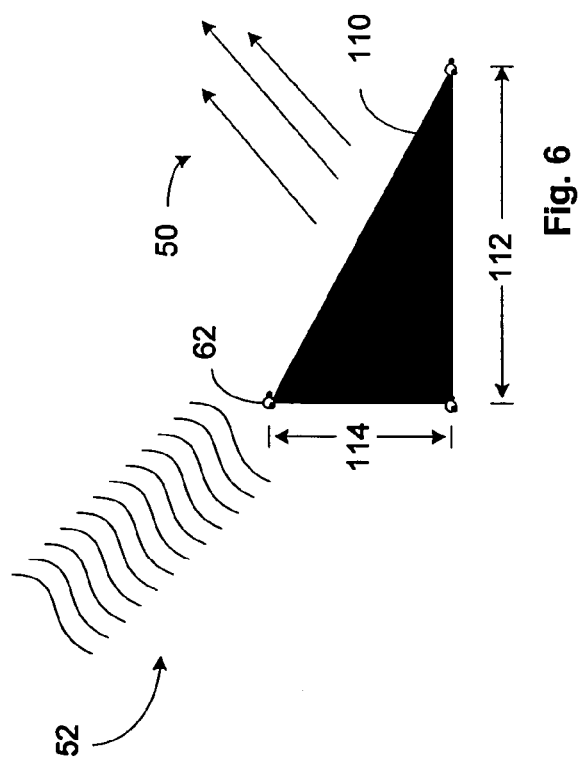
FIG. 6 illustrates a triangular metal shape undergoing enhanced Raman scattering due to plasmon resonance.

Referring to FIG. 6, another enhancement mechanism utilizing metal particles of unusual geometries is illustrated. For example, a triangular metal particle 110 can be used to enhance Raman scattering. Each side of the triangular metal particle 110, for example, has a length 112 and a height 114 on the order of $\lambda/10$. The actual dimensions of the triangular metal particle 112 depend on the RAM resonant frequency, which exists over many wavelengths. RAMs 62 are placed along the triangular metal particle at varying intervals along its surface. As was described previously with respect to the metal nano-spheres, the concentration of RAMs can vary depending on the application requirements. The shape may be formed using conductive metals, such as silver, gold, copper and aluminum, for example. Additionally, the shape is not limited to a triangular shape, but may be any shape, such as a rectangle, polygon, hexagon, etc.

Incident optical radiation 52 excites plasmons at different points on the triangular metal particle 110. The excited plasmons produce an electric field on the surface of the metal particle 110, and RAMs 62 within the electric field increase their Raman emissions, thereby producing enhanced Raman scattering 50.

The previously described enhancement mechanisms increase Raman emissions through plasmon resonance. In an alternative embodiment, the enhancement mechanism increases Raman emissions by increasing the number of final states of the system. Increasing the final states of the system reaches the same goal as that obtained by plasmon resonance. That is, the RAM is placed in a strong electric field. Just as plasmon resonance produces a strong electric field, increasing the density of states also produces a strong electric field. Regardless of the method of creating the strong electric field, Raman active scattering is increased when a RAM is subject to the strong electric field.

Enhanced Raman scattering can be achieved utilizing photonic crystals, which increase Raman emissions by increasing the number of final states of the system, which increases the electric field intensity. Photonic crystals are artificially 3-dimensional (or 2- or 1-dimensional) structures fabricated in an optical material (crystal or amorphous) with unit cells whose dimensions are comparable to the optical wavelength. If the artificial structure has appropriate symmetry, it can exhibit a photonic bandgap forming what is called a photonic bandgap (PBG) material or crystal. This bandgap in the photon energies is analogous to electron bandgaps in semiconductors. Thus, photonic crystals are periodic dielectric structures that have a bandgap that forbids propagation of a certain frequency range of light. This property enables one to control light and produce effects that are impossible with conventional optics. PBG materials exhibit characteristic frequency bands in which the density of states (i.e., the spectrum of the number of energy levels per eV versus energy) for electromagnetic wave propagation approaches zero. The length scale, symmetry, and dielectric constant contrast of the crystal structure define the domain and directionality of this bandgap.

Figure 7A:
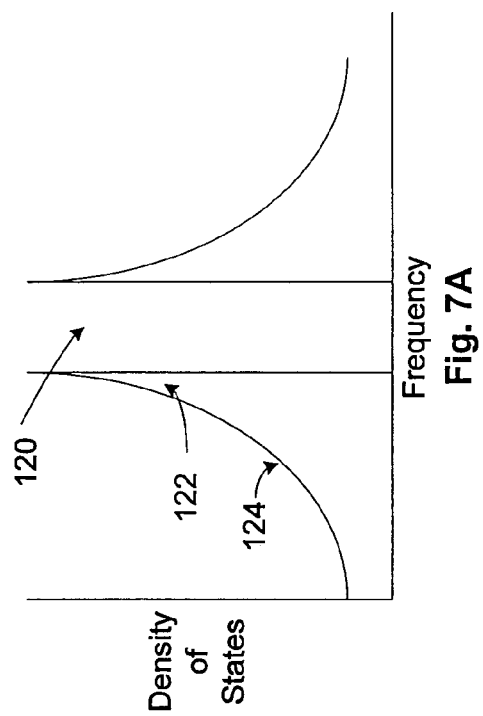
FIG. 7A is a graphical diagram illustrating the placement of a Raman active molecule relative to the photonic bandgap such that the density of states is increased.

Referring to FIG. 7A, a first method of enhancing Raman scattering through photonic crystals is to place a RAM just outside the photonic bandgap 120, i.e., the intervals of prohibited frequencies, such that the density of states is increased. The density of states is higher in a region 122 just outside the photonic bandgap 120 and near the curve 124. Therefore, the RAM is placed in the region 122 near the photonic bandgap 120 and the curve 124. An increase in the density of states results in an increase the scattering cross section of the photonic crystal. Since the scattering cross section is increased, Raman emissions from the photonic crystal also are increased. In order to achieve enhanced Raman scattering, the photonic bandgap is selected such that the Raman signal is outside the gap.

Figure 7B:
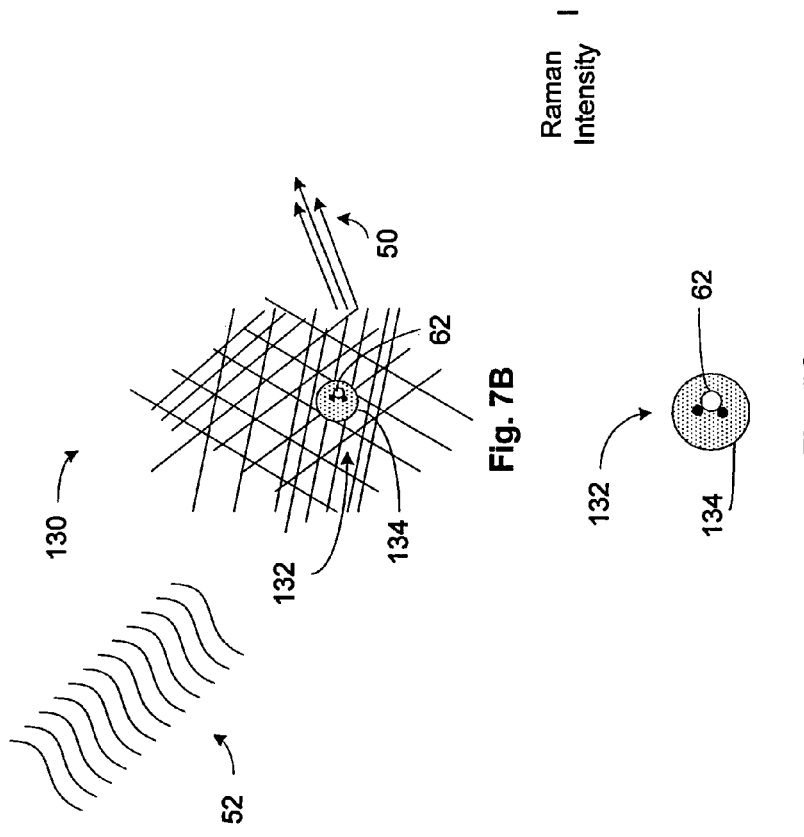
FIG. 7B is a schematic diagram of a photonic crystal having a defect undergoing enhanced Raman scattering.
Figure 7C:
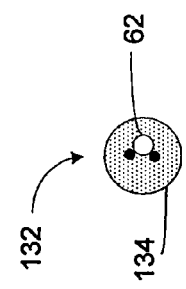
FIG. 7C illustrates the defect of the photonic crystal of FIG. 7B.

A second method of enhancing Raman scattering through photonic crystals is to create defects in the photonic crystal and place RAMs inside the defects. As in the previous embodiment, the photonic bandgap is selected such that the Raman signal is outside the gap. Referring to FIGS. 7B and 7C, a photonic crystal 130 having a defect 132 is illustrated. The defect, for example, is a defect cavity 134 within the photonic crystal 130. The defect 132 causes the electric field to resonate, thus increasing the strength the electric field. More simply, the defect 132 concentrates the electric field of the incident optical radiation 52 and therefore increases the scattering cross section of the RAM 62. Thus, an increase in Raman emissions is due to two factors. First, the concentrated electric field induces RAMs 62 within the range of the electric field to increase their Raman emissions. Second, the increased scattering cross section of the photonic crystal 130 produces more Raman emissions per unit area.

Figure 7D:
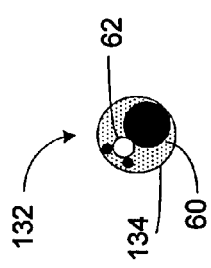
FIG. 7D illustrates the defect of the photonic crystal of FIG. 7B with a metal nano-sphere inside the defect.

Additionally, photonic crystals can be combined with plasmon resonance to produce an additive effect, thereby achieving a level of enhanced Raman scattering that is beyond what is achievable with each technique standing alone. With further reference to FIG. 7D, a metal nano-sphere 60, for example, can be placed inside the defect cavity 134. As the photonic crystal 130 is subjected to optical radiation 52, the photonic crystal 130, as described above, undergoes enhanced Raman scattering due to the increased scattering cross section of the photonic crystal 130 and due to the concentrated electric field within the defect. Additionally, the metal nano-sphere 60, as described previously, undergoes plasmon resonance, which also creates a strong electric field. Therefore, two independent electric fields are generated substantially simultaneously. These fields have an additive effect, thereby creating a stronger electric field than would be found from each method operating independently. The stronger field produces increased Raman emissions when compared to a weaker field, and thus the total Raman scattering is increased.

As described above, enhanced Raman scattering can be triggered from optical radiation, which, as is known in the art, can be generated from a laser source. One example of an acceptable laser source is an Nd:YAG laser with an output of 532 nanometers (nm). The Raman shifted spectra resulting from the 532 nm excitation fall within the peak responsivity region of silicon CCD (charge coupled device) detectors. In certain instances, however, the 532 nm laser can cause sample fluorescence, which may swamp the Raman signal and thus make it difficult to detect or undetectable.

Another example of an acceptable laser source is a near infrared excitation source. A near infrared excitation source can eliminate sample fluorescence from most organic molecules. A wavelength of 785 nm has been found to be optimum for Raman spectroscopy applications, as it avoids fluorescence but still returns a Raman signal sufficient to enable detection by a CCD at a reasonable signal-to-noise ratio.

It is noted that while the above description illustrates a single type of RAM utilized in conjunction with an enhancement mechanism, different types of RAMs can be combined with the enhancement mechanism to provide a unique Raman signature. For example, a first type of RAM (M1) can be utilized in a first concentration, combined with a second type of RAM (M2) utilized with a second concentration, wherein the concentration of M2 is less than the concentration of M1, and so on. The combination of multiple types of RAMs produces a unique Raman signature that easily can be distinguished from other Raman signatures.

Figure 8:
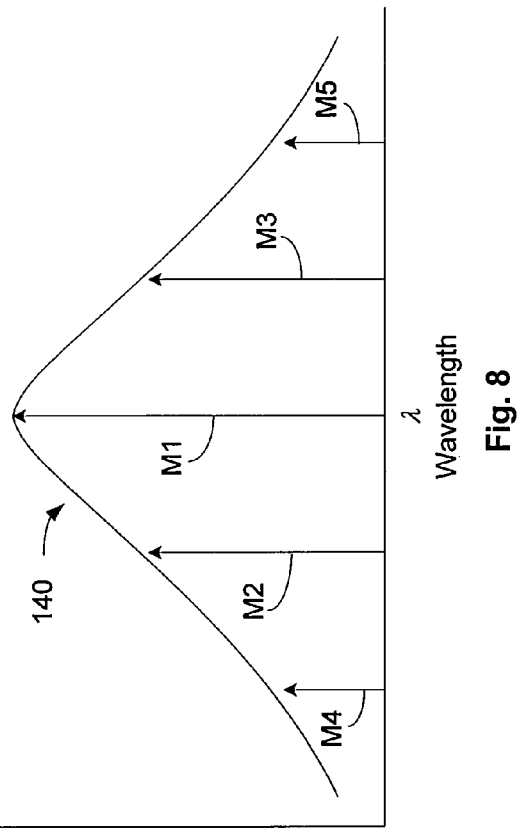
FIG. 8 is a graphical diagram illustrating the signature obtained from a combination of multiple types of RAMs.

Referring to FIG. 8, the above described concept is shown graphically for a blended group of RAMs, M1, M2, M3, M4 and M5. M1 has the highest concentration, followed by M2 and M3, which have concentrations substantially equal to each other, but less than the concentration of M1. M4 and M5 have concentrations substantially equal to each other, but less than the concentrations of M1, M2 and M3. The curve 140 represents the signature of the blended RAMs. It is noted that the curve is merely exemplary and any combination of RAMs in various concentrations can be combined without departing from the scope of the invention.

In light of the above described methods for increasing Raman emissions, an identification system now will be described implementing the above described methods.

Figure 9:
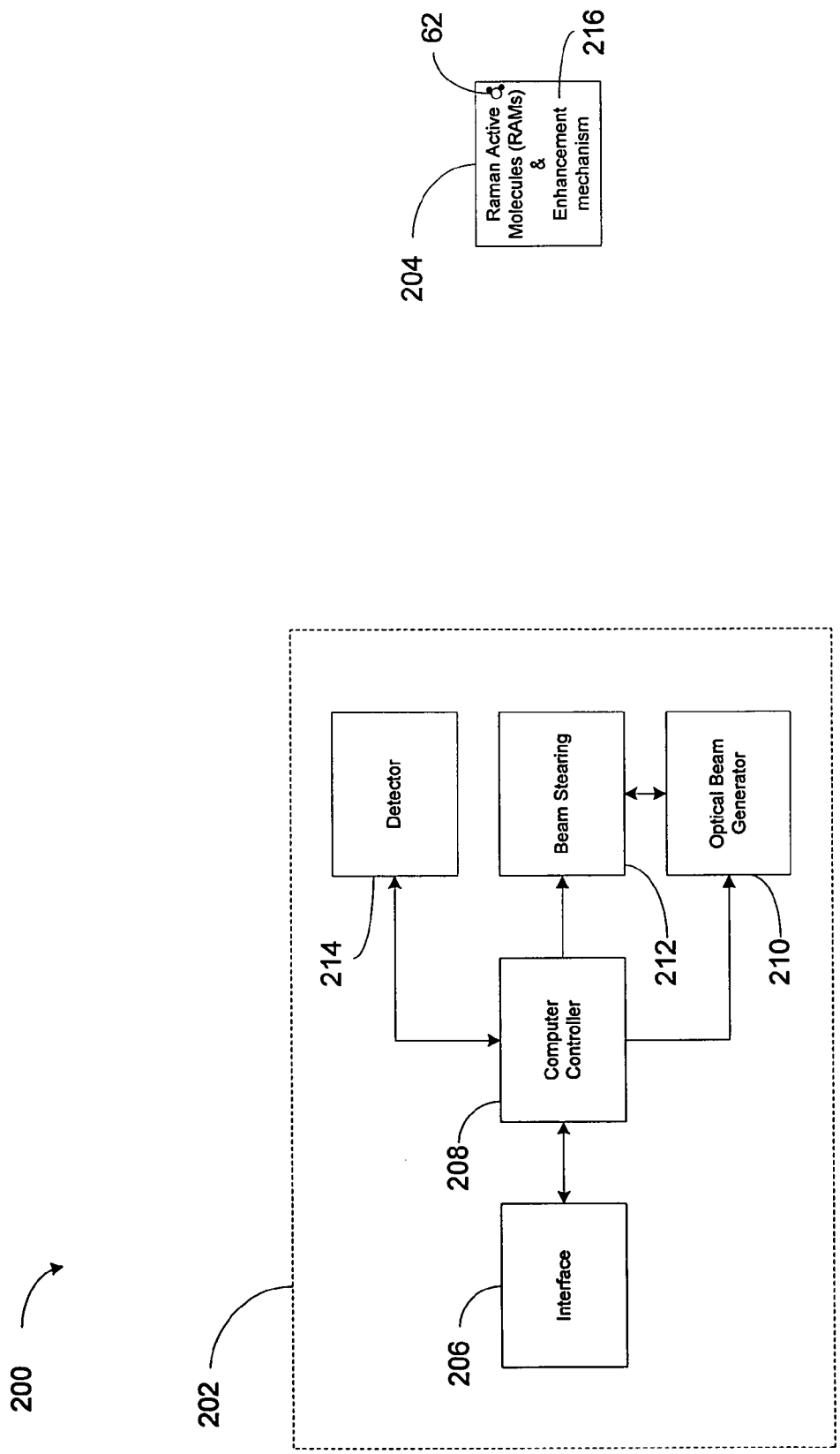
FIG. 9 is a block diagram of an identification system in accordance with an embodiment of the invention.

Referring to FIG. 9, an IFF system 200 in accordance with an embodiment of the invention is illustrated. The IFF system 200 includes an interrogator 202 and a marker 204. The interrogator 202, which is shown attached to an aircraft 20, can be attached to any weapons platform and/or vehicle that may fire upon a target. The marker 204, on the other hand, is attached only to "friendly" objects of interest. The marker 204, which is passive and does not require power to operate, includes the enhancement mechanism 216 and RAMs 62 as is described in more detail below.

In operation, the interrogator 202 transmits an optical beam toward an object of interest and receives a reflected signal therefrom. As the optical beam strikes an object having a marker 204 attached to its surface, enhanced Raman scattering will occur at the marker 204, and the scattering produces a signature that is unique for the particular marker 204. Conversely, as the beam strikes an object not having a marker 204 attached to its surface, enhanced Raman scattering does not occur or the signature produced by the scattering will not match a predetermined signature. The Raman signature is carried back to the interrogator 202 in the reflected signal and the interrogator 202, in accordance with the invention, classifies the object based on the Raman signature.

As shown in FIG. 9, the interrogator 202 includes an interface 206, a computer controller 208, an optical beam generator 210, a beam steering controller 212 and a detector 214 each of which will be described more fully below. The marker 204 includes a plurality of enhancement mechanisms 216 and a plurality of RAMs 62, as also will be described more fully below.

The components of the interrogator 202 will now briefly be discussed. The interface 206 provides a convenient means for operating the IFF system 200. The interface 206 includes an input device (not shown), such as a keyboard, a pointing device, a touch screen, etc., and an output device (not shown), such as a display, e.g., an LCD or a CRT display. Software executed by the computer controller 208 accepts commands from the interface 206, such as, for example, the area to be scanned, and provides feedback to the interface, such as the classification (friend or foe) of an object of interest and/or the status of the IFF 200, for example. The optical beam generator 210 and the beam steering controller 212 generate and position the optical beam on the desired object of interest. The computer controller 208 commands the optical beam generator 210 when to generate a beam and the computer controller instructs the beam steering controller 212 where the beam shall be directed. The detector 214 receives a reflected signal from the object of interest and provides the reflected signal to the computer controller 208. The computer controller analyzes the reflected signal and classifies the object of interest as a friend or foe based on the Raman effect.

Figure 10:
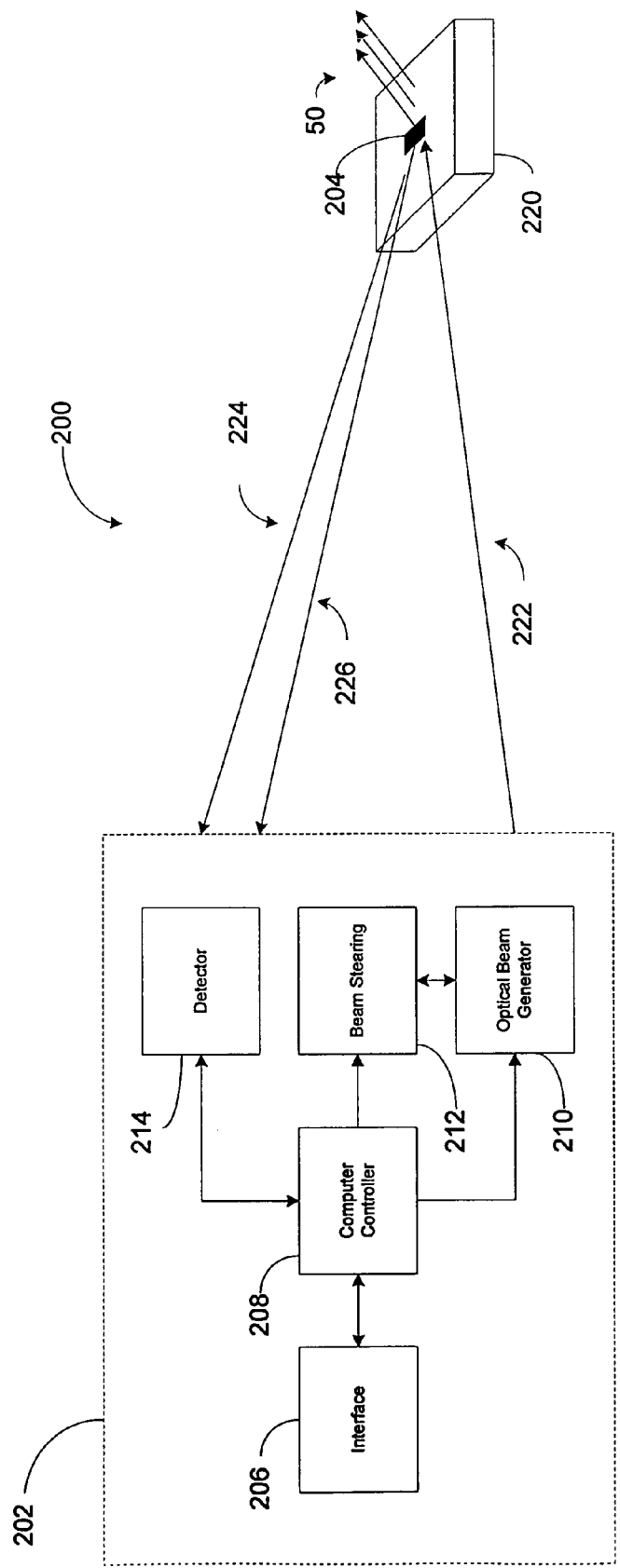
FIG. 10 is a block diagram of the identification system of FIG. 2 in operation.

With reference to FIG. 10, the IFF system 200 is shown in operation. The marker 204 is applied to an object 220 and the interrogator 202 emits an optical beam 222 towards the object 220. As the optical beam 222 strikes the marker 204, enhanced Raman scattering 50 occurs and a unique Raman signature is generated. A portion of the optical beam 222 is reflected back towards the interrogator 202. The reflected beam 224 includes a frequency shifted Raman return signal 226 that is generated at the surface of the marker 204. The detector 214 receives the reflected beam 224 including the Raman return signal 226 and provides the data to the computer controller 208. The computer controller 208 analyzes the data to determine whether the object 220 is a friend or foe. If the Raman signature, which is carried in the Raman return signal 226, matches a predetermined "friendly signature", then the object is designated as a friend. If, on the other hand, the Raman signature does not match a predetermined signature or the Raman return signal 226 is not present, the computer controller designates the object as a foe.

Raman signatures are derived empirically by generating a pre-measured set of Raman spectral signals. These signals are stored and later compared to the actual battle field measurements. For example, different types of RAMs are combined with an enhancing mechanism in different concentrations and a measurement of each Raman signature is recorded. Subsequently, another type of RAM is combined with an enhancing mechanism in different concentrations and a Raman signature is recorded. This process is repeated until a sufficient sample of Raman signatures is collected for the particular application. The records of each signature are stored on a computer, e.g., the computer controller 208. When actual measurements are taken in the battlefield, the computer compares the stored signals to the actual measured signal and determines if the actual measured signal matches a pre-measured signal.

Figure 11:
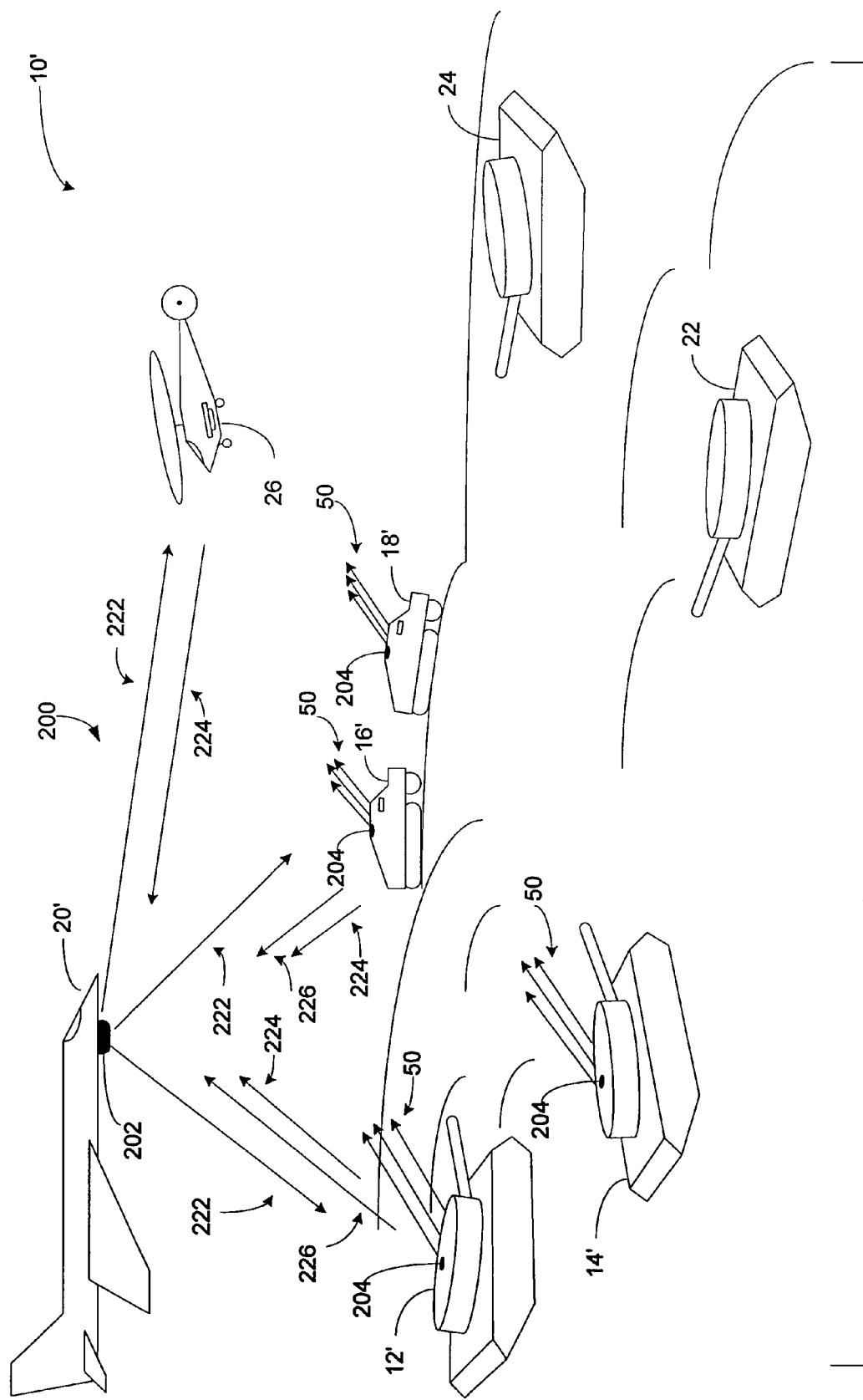
FIG. 11 is a representation of a battlefield environment in which an identification friend-or-foe system in accordance with an embodiment of the invention is employed.

Referring to FIG. 11, a battlefield 10' is illustrated wherein the IFF system 200 is shown being used in a battle situation. The interrogator 202 is mounted on an attack plane 20', for example, while a marker 204 is attached to each friendly vehicle, such as the first tank 12', the second tank 14', the first personnel carrier 16', and the second personnel carrier 18'. It will be appreciated that the interrogator 202 may be mounted on other vehicles, such as, for example, a tank or personnel carrier, and its placement on the attack plane 20' is merely exemplary. Furthermore, although a single marker 204 is shown attached to each friendly vehicle, it will be appreciated that a plurality of markers may be attached to each vehicle. Markers can be applied to the top, side, front and back surface, or any surface required to allow identification from various vantage points.

As described above, the interrogator 202 emits an optical beam 222 towards each object of interest. Objects that have a marker 204 attached to their surface will undergo enhanced Raman scattering 50 at the marker surface, while objects that do not have a marker 204 either will not undergo enhanced Raman scattering or will have Raman scattering that has a signature that does not match a predetermined signature. The reflected beam 224 and, if present, the Raman return signal 226 travel back toward the interrogator 202. The detector 214 receives the reflected signal and provides data regarding the signal to the computer controller 208. The computer controller 208 processes the data to retrieve the Raman signature and, based on the Raman signature, determines whether the object is a friend or foe and reports the determination to the interface 206.

Figure 12:
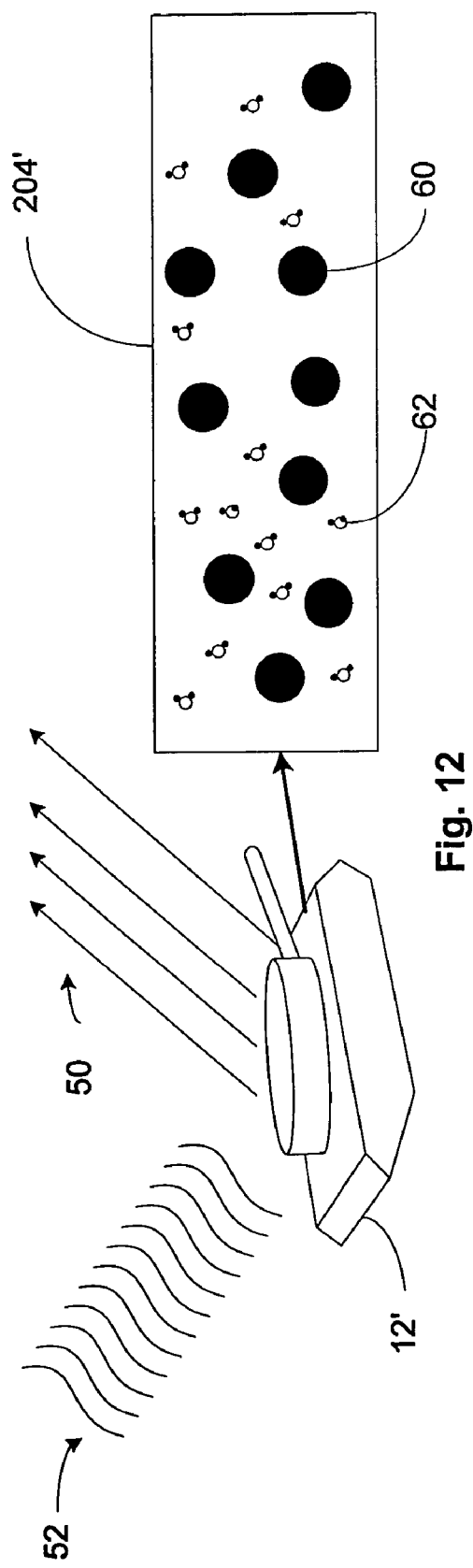
FIG. 12 is a schematic diagram illustrating metal nano-spheres and Raman active molecules on a decal in accordance with another embodiment of the invention.

As stated above, the marker 204 is attached and/or applied to objects that are designated as friendly. The marker 204 may be attached and/or applied using any medium that facilitates the application and removal of the marker 204. Referring to FIG. 12, a thin layer of material, such as a decal 204', can be used as the marker 204, for example. The decal 204' is applied to an object, such as the tank 12', and includes, for example, a transparent material containing metal nano-spheres 60 and RAMs 62. Alternatively, the marker may be applied to the surface of an object as a coating, such as a spray coating, for example. It will be appreciated that other methods of attaching and/or applying the marker 204 to an object may be used.

The marker is created, for example, by embedding RAMs 62 and metal nano-spheres 60 on a common base, e.g., an adhesive sheet. It will be appreciated that other enhancement mechanisms listed herein can be embedded on the marker, and the use of metal nano-spheres is merely exemplary. The sheet and the adhesive should be formed to withstand the effects of the surrounding environment, taking into account that the marker will be subject to varying atmospheric conditions (e.g., temperature, moisture, etc.). Satisfactory materials for the sheet and adhesive include any material that is transparent to the chosen RAM spectrum as well as the interrogation spectrum. The RAMs and metal nano-spheres are embedded on the sheet by combining and adding them to the sheet at the same time. Similarly, when the marker is applied in a spray form, the RAMs and the enhancing mechanism are combined in a sprayable coating and then applied to the surface to be marked.

In an alternative embodiment, the invention may be used to detect the presence (or lack thereof) of biological and/or chemical agents in a region. During war, biological and/or chemical attacks are a significant possibility. Thus, it is desirable to detect the biological and/or chemical agents prior to friendly forces entering the region. The presence of biological and/or chemical agents may be detected using the Raman effect discussed herein. By analyzing the Raman scattering in a suspect region, a determination can be made as to the presence of biological and/or chemical agents.

Figure 13:
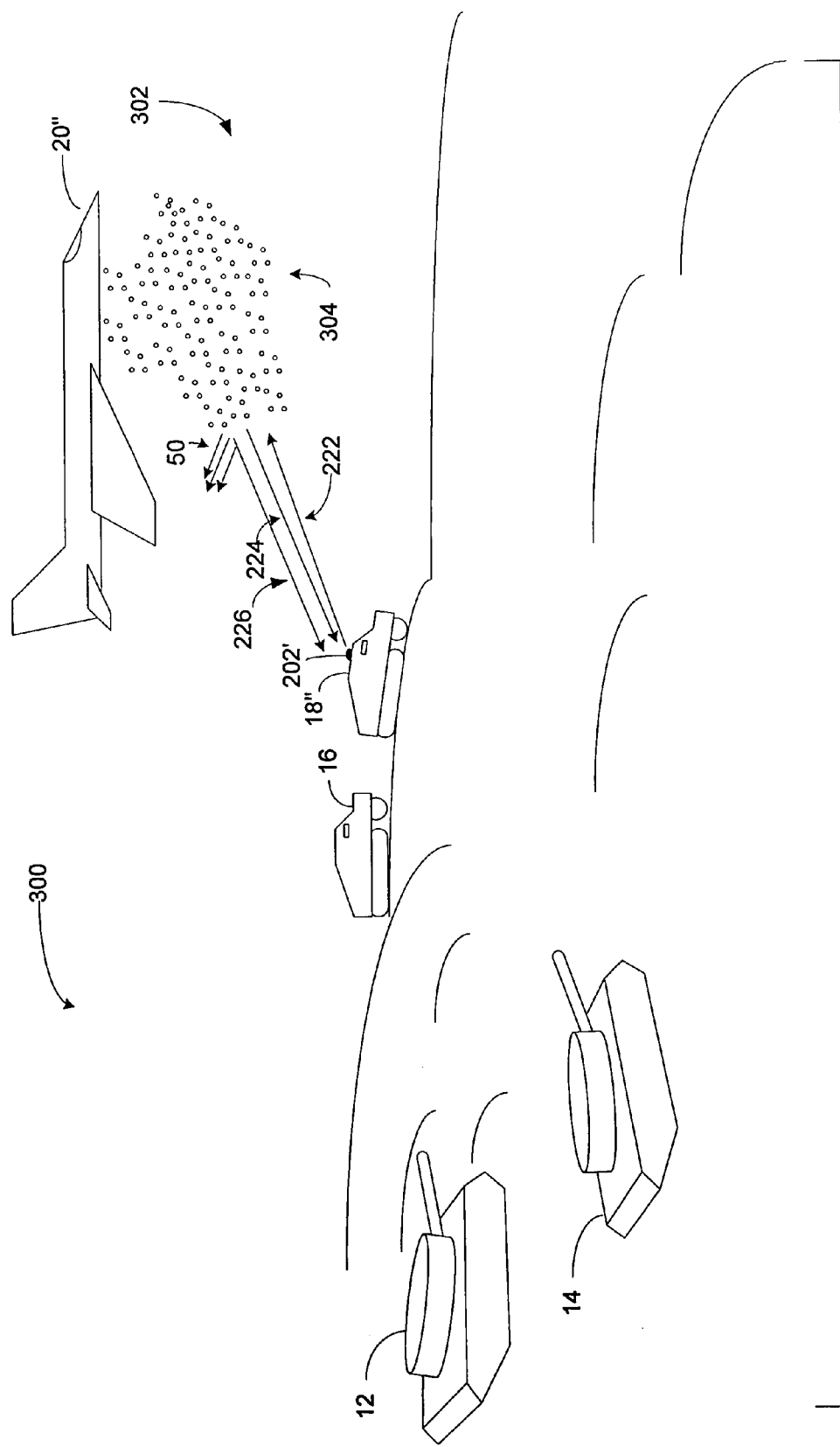
FIG. 13 is a representation of a battlefield environment in which a biological and/or chemical identification system in accordance with another embodiment of the invention is employed.

Referring to FIG. 13, a battlefield 300 is illustrated. The battlefield 300 includes friendly forces, such as a first tank 12, a second tank 14, a first personnel carrier 16 and a second personnel carrier 18". Ahead of the friendly forces is a suspect region 302 in which biological and/or chemical agents may be present. Prior to entering the suspect region 302, an interrogator 202', which, for example, is mounted on the second personnel carrier 18", emits an optical beam 222 toward the suspect region 302. As airborne matter, such as biological and/or chemical agents, are struck by the optical beam 222, Raman scattering occurs. A portion of the beam 224 is reflected back towards the interrogator 202', including a Raman return signal 226 (which includes the Raman signature).

Under normal conditions, the Raman emissions from any biological and/or chemical agents in the region are low and difficult to detect. The Raman emissions, however, can be enhanced using an enhancement mechanism 304. The enhancement mechanism is dispersed over the suspect region 302 by an aircraft 20", for example. It will be appreciated that other means of disbursing the enhancement mechanism 304 may be used, such as, for example, a helicopter and/or a projectile. The enhancement mechanism 304 can be dispersed as individual particles into the atmosphere or, alternatively, a carrier (not shown) can be used to disperse the enhancement mechanism 304 in the suspect region 302. The enhancement mechanism 304 may be a mechanism described previously in this disclosure. For example, the enhancement mechanism 304 can be metal nano-spheres, concentric rings, photonic crystals, etc. The concentration of the enhancement mechanism deployed into the atmosphere depends on the concentration of the biological/chemical agent in the atmosphere. As the concentration of the biological/chemical agent decreases, the concentration of the enhancement mechanism increases. As will be described below, if a collector is used to concentrate the biological/chemical agents, then the concentration of enhancement particles needed to enhance the Raman scattering can be reduced.

In operation, the aircraft 20" disperses the enhancement mechanism 304 over the suspect region 302. Biological and/or chemical agents in the region attach themselves to the enhancement mechanism 304 by collisions in the air. As the optical beam 222 strikes the enhancement mechanism 304, plasmon resonance, for example, occurs on the surface of the enhancement mechanism 304. The plasmon resonance, as described above, creates a strong electric field near the surface of each enhancement mechanism 304, and RAMs within the range of the field undergo enhanced Raman scattering 50. The presence of biological and/or chemical agents attached to the enhancement mechanism 304 will produce a unique Raman signature, thereby facilitating the identification of biological and/or chemical agents in the suspect region 302. It will be appreciated by those having ordinary skill in the art that the Raman signature of various biological and/or chemical compounds may be obtained empirically. After receiving the Raman signature, the interrogator classifies the airborne matter as safe or hazardous by comparing the signature to known signatures of hazardous matter.

Figure 14:
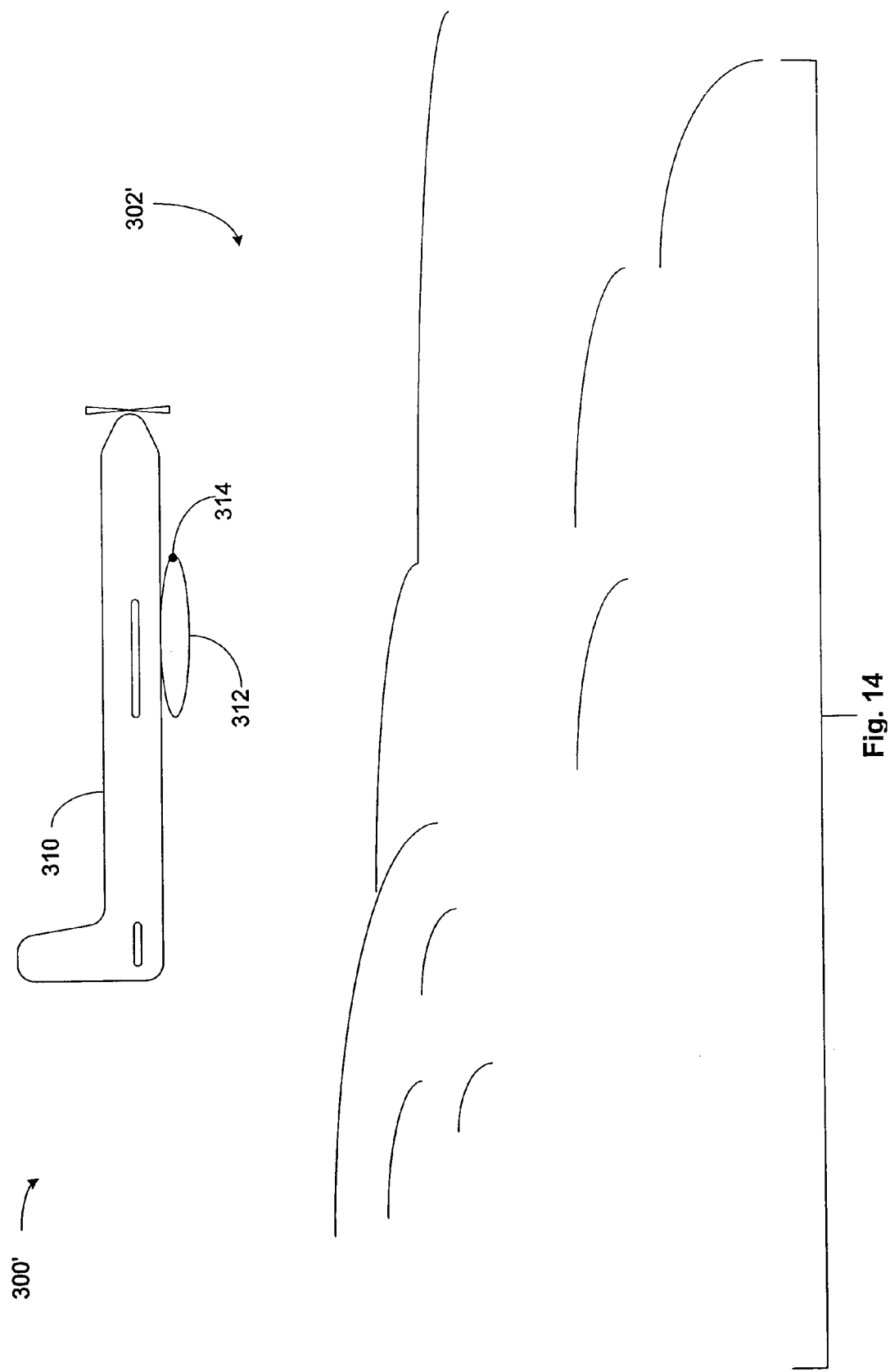
FIG. 14 is a representation of a battlefield environment in which a biological and/or chemical identification system in accordance with another embodiment of the invention is employed.

Referring to FIG. 14, an alternative embodiment for detecting biological and/or chemical agents in a region is illustrated. By sampling and analyzing air in a suspect region 302', a determination can be made as to whether biological and/or chemical agents are present in the suspect region 302'.

A remotely controlled plane 310, which also may be referred to as a drone 310, flies over the suspect region 302' of a battlefield 300'. Remote controlled aircraft are widely known by those having ordinary skill in the art of drone aircraft and will not be discussed herein. A collector 312, which is attached to the drone 310, includes an inlet 314 that permits a flow of air to enter the collector 312. As the drone 310 flies through the suspect region 302', air enters the inlet 314 and is sampled and concentrated by the collector for analysis. As will be described in more detail below, a Raman signature is obtained from the air sample and a determination is made as to the presence of biological and/or chemical agents in the sampled air.

Figure 15:
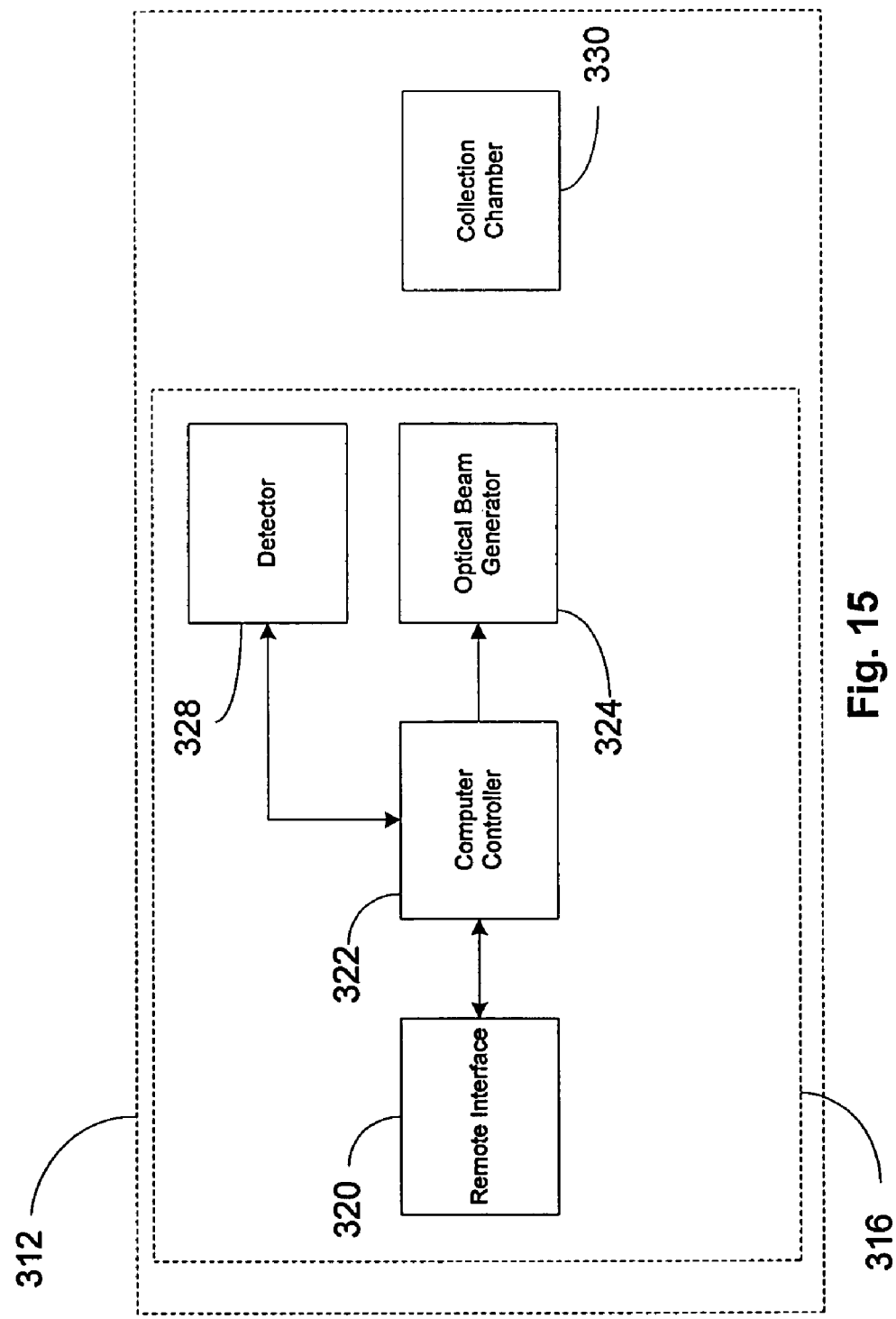
FIG. 15 is a block diagram of a concentrator in accordance with another embodiment of the invention.

With further reference to FIG. 15, the collector 312 will be described in more detail. As will be understood from the discussion below, the collector 312 includes components from the interrogator 202, which is shown in FIG. 2. The collector 312, using the Raman effect, determines whether biological and/or chemical agents are present in sampled portions of air. The collector 312 includes an interrogator 316, which in turn includes a remote interface 320, a computer controller 322, an optical beam generator 324, and a detector 328. The collector 312 also includes a collection chamber 330, which concentrates the sample as well as bringing it closer to the interrogating signal.

The remote interface 320 receives commands from a controller (not shown) operated by a remote operator, who generally is a safe distance from the suspect region 302'. These commands include, for example, enable sampling, perform analysis, number of samples to take, etc. It will be appreciated by those skilled in the art that any number and/or type of commands may be transmitted to the remote interface and the examples listed are not intended to be limiting in any way. The transmission of commands and data may be by any medium that is appropriate for the intended use of the drone. For example, in domestic applications standard RF transmissions may be satisfactory. In military applications, however, a more secure means of transmission may be desirable.

After receiving a command from the controller, the remote interface 320 communicates the command to the computer controller 322. Similarly, the computer controller 322 can communicate data to the remote interface 320, and the remote interface transmits the data to the controller (not shown). The optical beam generator 324 generates the optical beam in the collection chamber 330 based on a command from the computer controller 322. The detector 328 receives a reflected signal from the collection chamber and provides the reflected signal to the computer controller 322. The computer controller analyzes the reflected signal and classifies the sample as being safe or hazardous based on the Raman signature from the sampled air. For example, the interrogator compares the Raman signature to known signatures of hazardous materials. If a "returned" signature matches the signature of a known hazardous material then the sample is classified as hazardous. If the signature does not match a known signature of a hazardous material, then the sample is classified as safe.

Figure 16A:
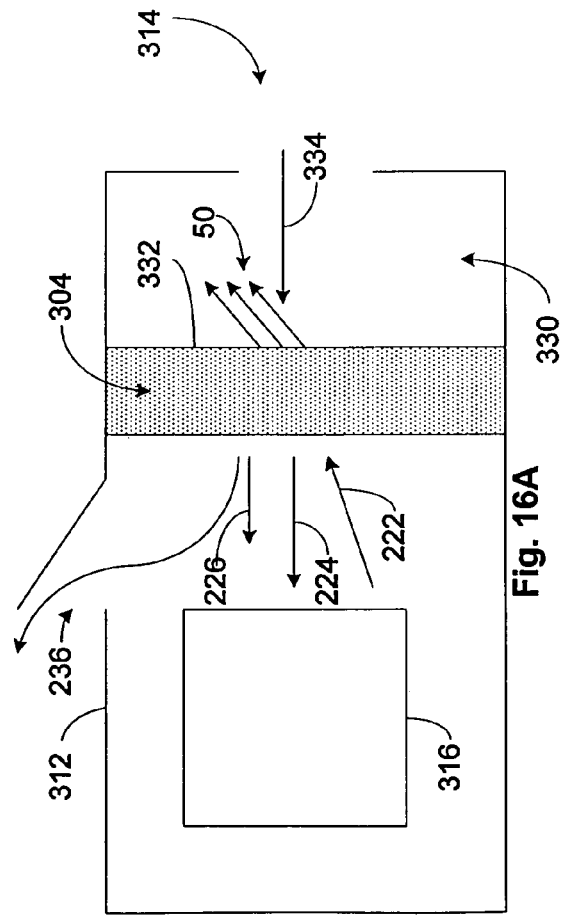
FIG. 16A is a schematic diagram of a concentrator in accordance with another embodiment of the invention.

The collection chamber 330 provides a means for collecting air from the suspect region 302' and analyzing that air. FIG. 16A illustrates an embodiment of the collector 312 along with the collection chamber 330. The collection chamber 330 includes a filter 332 for collecting samples of air from the suspect region 302'. The filter can be a standard biological/chemical agent filter used for filtering contaminated air. The filter 332 is embedded with an enhancement mechanism 304 that facilitates inducement of enhanced Raman scattering. The enhancement mechanism 204 may be any mechanism described herein, such as metal nano-spheres, concentric rings, photonic crystals, etc. The collection chamber 330 may include a filter changer (not shown) which automatically replaces the filter with a clean filter after each air sample is taken, for example.

As sampled air 334 enters the collection chamber 230 through the inlet 314, the air passes through the filter 332 and exits from an air outlet 336. Biological and/or chemical agents present in the air are trapped in the filter 332 and combine with the enhancement mechanism 304. An optical beam 222 generated by the interrogator 316 strikes the filter 332, inducing enhanced Raman scattering 50. If biological and/or chemical agents are present in the filter, the enhanced Raman scattering will produce a unique signature. A portion of the beam 224 along with a Raman return signal 226 is reflected towards the detector 328. The detector 328 receives the information and provides the data to computer controller 322. The computer controller 322 analyzes the data and, based on the Raman signature, determines whether biological and/or chemical agents are present in the suspect region 302'. The results of the analysis then are transmitted back to the controller (not shown).

Figure 16B:
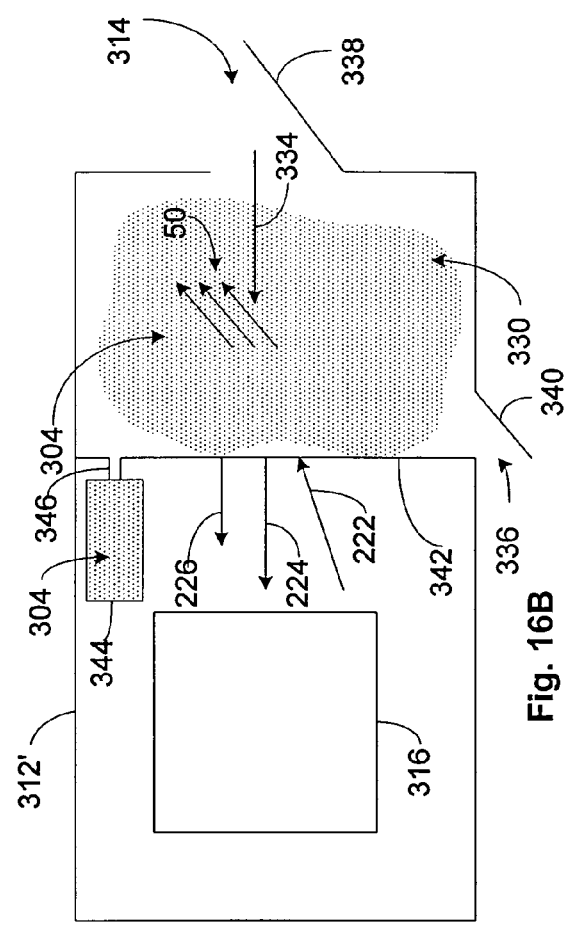
FIG. 16B is a schematic diagram of a concentrator in accordance with another embodiment of the invention.

Referring now to FIG. 16B, an alternative embodiment of the collector 312' is illustrated. An air inlet 314 allows sampled air 334 to enter the collection chamber 330. The air inlet 314 includes a door or sealing device 338, which allows the air inlet to be opened or closed. An air outlet 336 provides a means for the evacuation of air from the collection chamber and to make way for the next air sample 334. The air outlet 336 also includes a door 340, which allows the air outlet to be opened or closed. A divider 342 separates the collection chamber 330 from the remainder of the collector 312'. The divider is transparent and may be made from glass, for example. The interrogator 316 resides on one side of the divider 342, while the collection chamber 330 resides on the other side of the divider 342. A reservoir 344 is connected to the collection chamber 330 through a duct 346. The reservoir 344 contains a plurality of enhancement mechanisms 304, e.g., metal nano-spheres, concentric rings, photonic crystals, etc.

As the drone 310 carries the collector 312' into the suspect region 302', the inlet door 338 and the outlet door 340 are opened and air enters the collection chamber 330. When a sufficient sample has been taken, the inlet door 338 and the outlet door 340 are closed, thus sealing the collection chamber 330 from the outside atmosphere. Once the collection chamber 330 is sealed, the reservoir 344 injects a portion of the enhancement mechanism 304 through the duct 346 and into the collection chamber 330. The enhancement mechanism 304 may be injected using a pump and/or pressurized air (not shown), for example. Biological and/or chemical agents present in the sampled air 334 collide and combine with the enhancement mechanism 304. An optical beam 222 generated by the interrogator 316 strikes the enhancement mechanism 304, creating a strong electric field and inducing enhanced Raman scattering 50. If biological and/or chemical agents are present in the collection chamber 330, the enhanced Raman scattering will produce a unique signature. A portion of the beam 224 along with a Raman return signal 226 is reflected towards the detector 328. The detector 328 receives the information and provides the data to computer controller 322. The computer controller 322 analyzes the data and, based on the Raman signature, determines whether biological and/or chemical agents are present in the suspect region 302'. The results of the analysis then are transmitted back to the controller (not shown).

It will be appreciated that although the invention has been shown attached to a vehicle and an aircraft, the invention may be produced as a hand-held and/or field portable device. For example, the interrogator may be scaled down to a hand-held device. The interface may include a membrane keypad and an LCD screen, while the computer controller is implemented on a single board. The associated laser emission and detection components may be included within the interrogator.

While particular embodiments of the invention have been described in detail, it is understood that the invention is not limited correspondingly in scope, but includes all changes, modifications and equivalents coming within the spirit and terms of the claims appended hereto. For example, the detection range of the system further may be increased by using optical enhancement tools. A telescope (not shown), for example, may be connected to the detector 64 (FIG. 2) to increase the range of detection.

What is claimed is:

1. A system for increasing Reman emissions from a plurality of Raman active molecules (RAMs) corresponding to an object of interest, and making an identification therefrom, comprising:
   an enhancement mechanism, wherein the enhancement mechanism enhances Raman scattering from the plurality of Raman active molecules (RAMs); and
   an interrogator for transmitting a signal toward the object of interest and receiving a return signal therefrom, wherein the return signal includes a Raman signature, and the interrogator classifies the object as friend or foe based on the Raman signature.

2. The system of claim 1, wherein the enhancement mechanism enhances a local electric field about the enhancement mechanism.

3. The system of claim 2, wherein the electric field is enhanced by plasmon resonance.

4. The system of claim 1, wherein the interrogator includes a near infra-red excitation source.

5. The system of claim 4, wherein the near infra-red excitation source has a wavelength of about 785 nanometers.

6. The system of claim 1, further comprising:
at least one marker, wherein the marker includes a plurality of Raman active molecules (RAMs) and the enhancement mechanism.

7. The system of claim 6, wherein the interrogator comprises
an optical generator for generating and transmitting an optical beam;
a computer controller for directing the optical beam toward an object; and
a receiver for receiving the return signal.

8. The system of claim 6, wherein the marker comprises a decal, and the enhancement mechanism and the RAMs are embedded on the decal.

9. The system of claim 6, wherein the marker comprises a coating, and the enhancement mechanism and the RAMs are mixed in the coating.

10. The system of claim 9, wherein the coating is applied as a spray.

11. The system of claim 6, wherein the marker is passive.

12. A system for increasing Raman emissions from a plurality of Raman active molecules (RAMs) corresponding to an object of interest, and making an identification therefrom, comprising:
an enhancement mechanism comprising a plurality of photonic crystals, wherein the enhancement mechanism enhances Raman scattering from the plurality of Raman active molecules (RAMs); and
an interrogator for transmitting a signal toward the object of interest and receiving a return signal therefrom, wherein the return signal includes a Raman signature, and the interrogator classifies the object based on the Raman signature.

13. The system of claim 12, wherein the plurality of photonic crystals are selected to have a photonic bandgap such that a Raman signal is outside the photonic bandgap.

14. The system of claim 13, wherein the photonic crystals include at least one defect and at least one Raman active molecule is placed inside the defect.

15. The system of claim 14, wherein the defect is a cavity within at least one photonic crystal.

16. The system of claim 14, further comprising:
a second enhancement mechanism, wherein the second enhancement mechanism is placed inside the at least one defect.

17. The system of claim 13, wherein the RAMs are placed outside the photonic bandgap.

18. The system of claim 17, wherein the RAMs are placed such that the density of states is increased.

19. The system of claim 12, wherein the interrogator classifies the object as safe or hazardous.

20. The system of claim 19, wherein the enhancement mechanism is dispersed over a suspect region, and the enhancement mechanism attaches to suspect particles in the suspect region.

21. The system of claim 19, further comprising:
a collector, wherein the collector samples air from a suspect region and combines the air with the enhancement mechanism.

22. The system of claim 21, wherein the collector includes a filter and the filter combines the air with the enhancement mechanism.

23. The system of claim 22, wherein the enhancement mechanism is embedded within the filter.

24. The system of claim 21, wherein the collector is carried into the suspect region by an unmanned device.

25. The system of claim 21, wherein the collector includes an air inlet and an air outlet.

26. The system of claim 25, further comprising:
a reservoir, wherein the reservoir stores the enhancement mechanism and releases a portion of the enhancement mechanism when a new air sample is taken.

27. The system of claim 25, wherein the air inlet and the air outlet include a sealing mechanism which prevents air from entering and exiting the collector.

28. A method for increasing Raman emissions from a plurality of Raman active molecules (RAMs) corresponding to an object of interest, and making an identification therefrom, comprising the steps of:
providing an enhancement mechanism comprising a plurality of photonic crystals, wherein the enhancement mechanism enhances Raman scattering from the plurality of Raman active molecules (RAMs);
creating a local electric field about the enhancement mechanism to induce enhanced Raman scattering; and
classifying the object based on a Raman signature produced by the enhanced Raman scattering.

29. The method of claim 28, wherein the plurality of photonic crystals are selected to have a photonic bandgap such that a Raman signal is outside the photonic bandgap.

30. The method of claim 29, wherein the step of providing a plurality of photonic crystals includes using photonic crystals that include at least one defect and placing at least one Raman active molecule inside the defect.

31. The method of claim 30, wherein the step of using photonic crystals that include at least one defect includes forming the defect as a cavity.

32. The method of claim 30, further comprising the steps of:
selecting a second enhancement mechanism; and
placing the second enhancement mechanism inside the at least one defect.

33. The method of claim 29, further comprising the step of:
placing a plurality of RAMs outside the photonic bandgap.

34. The method of claim 33, wherein the step of placing the plurality of RAMs outside the photonic bandgap includes placing the RAMs such that the density of states is increased.

35. The method of claim 28, further comprising the step of:
applying at least one marker to an object, wherein the marker includes a plurality of RAMs and the enhancement mechanism.

36. The method of claim 35, wherein the step of applying at least one marker to an object includes using an adhesive to apply the marker.

37. The method of claim 35, wherein the step of applying at least one marker to an object includes spraying the marker on the object.

38. The method of claim 28, wherein the step of classifying an object based on a Raman signature includes classifying the object as safe or hazardous.

39. The method of claim 38, further comprising the step of:
collecting air samples from a suspect region; and
combining the air sample with the enhancement mechanism.

40. A method for increasing Raman emissions from a plurality of Raman active molecules (RAMs) corresponding to an object of interest, and making an identification therefrom, comprising the steps of:

providing an enhancement mechanism, wherein the enhancement mechanism enhances Raman scattering from the plurality of Raman active molecules (RAMs);

creating a local electric field about the enhancement mechanism to induce enhanced Raman scattering; and classifying the object based on a Raman signature produced by the enhanced Raman scattering, wherein the step of classifying an object based on a Raman signature includes classifying the object as friend or foe.

41. The method of claim 40, wherein the step of creating a local electric field about the enhancement mechanism includes inducing plasmon resonance to enhance the local electric field.

42. The method of claim 40, wherein the step of creating a local electric field about the enhancement mechanism includes using a near infra-red excitation source.

43. The method of claim 33, wherein the step of using a near infra-red excitation source includes using an excitation source having a wavelength of about 785 nanometers.

44. A method for increasing Raman emissions from a plurality of Raman active molecules (RAMs) and making an identification therefrom, comprising the steps of:

providing an enhancement mechanism, wherein the enhancement mechanism enhances Raman scattering from the plurality of Raman active molecules (RAMs);

creating a local electric field about the enhancement mechanism to induce enhanced Raman scattering; and classifying an object based on a Raman signature produced by the enhanced Raman scattering, wherein the step of classifying an object based on a Raman signature includes classifying the object as safe or hazardous, and, wherein the step of providing an enhancement mechanism includes dispersing the enhancement mechanism over a suspect region.

45. A method for increasing Raman emissions from a plurality of Raman active molecules (RAMs) and making an identification therefrom, comprising the steps of:

providing an enhancement mechanism, wherein the enhancement mechanism enhances Raman scattering from the plurality of Raman active molecules (RAMs);

collecting air samples from a suspect region;

combining the air samples with the enhancement mechanism;

creating a local electric field about the enhancement mechanism to induce enhanced Raman scattering;

classifying an object based on a Raman signature produced by the enhanced Raman scattering, wherein the step of classifying the object based on a Raman signature includes classifying the object as safe or hazardous, and the step of collecting air samples includes trapping airborne matter in a filter.

46. The method of claim 45, wherein the step of trapping the airborne matter in a filter includes using a filter having the enhancement mechanism embedded in the filter.

47. A method for increasing Raman emissions from a plurality of Raman active molecules (RAMs) and making an identification therefrom, comprising the steps of:

providing en enhancement mechanism, wherein the enhancement mechanism enhances Raman scattering from the plurality of Raman active molecules (RAMs);

collecting air samples from a suspect region;

combining the air samples with the enhancement mechanism;

creating a local electric field about the enhancement mechanism to induce enhanced Raman scattering;

classifying an object based on a Raman signature produced by the enhanced Raman scattering, wherein the step of classifying the object based on a Raman signature includes classifying the object as safe or hazardous, and the step of collecting air samples includes using an unmanned device to travel into the suspect region.

* * * * *